US012564375B2

(12) United States Patent
Xi et al.

(10) Patent No.: US 12,564,375 B2
(45) Date of Patent: Mar. 3, 2026

(54) DEVICES, SYSTEMS, AND METHODS FOR SECURELY AND SELECTIVELY ATTACHING AN ULTRASOUND ACCESSORY TO AN ENDOSCOPE

(71) Applicant: ENDOSOUND, INC., Portland, OR (US)

(72) Inventors: Jiefeng Xi, Nanjing (CN); Xianjie Su, Nanjing (CN); Yan Li, Nanjing (CN); Xunyi Li, Nanjing (CN); Scott Sutherland Corbett, III, Portland, OR (US); Jeremy Andrew Hammer, Portland, OR (US); Peter D. Hoffman, Portland, OR (US)

(73) Assignee: ENDOSOUND, INC., Portland, OR (US)

( * ) Notice: Subject to any disclaimer, the term of this patent is extended or adjusted under 35 U.S.C. 154(b) by 25 days.

(21) Appl. No.: 18/851,950

(22) PCT Filed: Apr. 19, 2023

(86) PCT No.: PCT/US2023/019069
§ 371 (c)(1),
(2) Date: Sep. 27, 2024

(87) PCT Pub. No.: WO2023/205211
PCT Pub. Date: Oct. 26, 2023

(65) Prior Publication Data
US 2025/0213215 A1 Jul. 3, 2025

(30) Foreign Application Priority Data
Apr. 21, 2022 (CN) ........................ 202220976227.X

(51) Int. Cl.
*A61B 8/00* (2006.01)
*A61B 8/12* (2006.01)

(52) U.S. Cl.
CPC .............. *A61B 8/12* (2013.01); *A61B 8/4411* (2013.01)

(58) Field of Classification Search
CPC ....... A61B 8/12; A61B 8/4411; A61B 8/0841; A61B 8/085; A61B 8/4444; A61B 1/018
See application file for complete search history.

(56) References Cited

U.S. PATENT DOCUMENTS 8,038,604 B2 * 10/2011 Hamazaki .......... A61B 1/00089
600/129
2011/0060187 A1 3/2011 Belafsky et al.
(Continued)

FOREIGN PATENT DOCUMENTS

CN 217310362 U 8/2022
WO 2023205211 A1 10/2023

OTHER PUBLICATIONS

International Search Report and Written Opinion for corresponding International Application No. PCT/US2023/019069 mailed Aug. 29, 2023.

*Primary Examiner* — Amal Aly Farag
(74) *Attorney, Agent, or Firm* — K&L Gates LLP

(57) ABSTRACT

A sleeve configured to be dispositioned between an endoscope and an ultrasound accessory selectively attachable to the endoscope is disclosed herein. The sleeve can include a rigid body configured to maintain a structural integrity of the sleeve, a first flexible layer positioned about an inner surface of the rigid body, and a second flexible layer positioned about an outer surface of the rigid body. The first flexible layer can create a friction fit between the inner surface of the rigid body and an outer surface of the endoscope and the second flexible layer can create a friction fit between the outer surface of the rigid body and the ultrasound accessory. The sleeve can be inserted into an inner bushing that includes a connecting plate configured for alignment with a
(Continued)

positioning plate of the ultrasound accessory such that the ultrasound accessory is properly positioned when selectively attached to the endoscope.

13 Claims, 10 Drawing Sheets

(56)          References Cited

U.S. PATENT DOCUMENTS

| | | |
|---|---|---|
| 2013/0046138 A1 | 2/2013 | McLawhorn |
| 2013/0137990 A1* | 5/2013 | Tsuruta .............. A61B 1/00087 |
| | | 600/466 |
| 2014/0296629 A1 | 10/2014 | Chang et al. |
| 2019/0208998 A1* | 7/2019 | Powers .............. A61B 1/00186 |
| 2021/0030261 A1* | 2/2021 | Kress ................... A61B 1/0125 |
| 2021/0212662 A1 | 7/2021 | Steinberg et al. |

* cited by examiner

4006

4004

4002

110

DEVICES, SYSTEMS, AND METHODS FOR SECURELY AND SELECTIVELY ATTACHING AN ULTRASOUND ACCESSORY TO AN ENDOSCOPE

CROSS-REFERENCE TO RELATED APPLICATIONS

This application is a U.S. National Stage Entry under 35 U.S.C. § 371 of International Patent Application No. PCT/US2023/019069, entitled DEVICES, SYSTEMS, AND METHODS FOR SECURELY AND SELECTIVELY ATTACHING AN ULTRASOUND ACCESSORY TO AN ENDOSCOPE, filed Apr. 19, 2023, which claims priority to Chinese Patent Application No. 202220976227.X, entitled "INNER BUSHING AND ULTRASONIC ENDOSCOPE", filed with the China National Intellectual Property Administration (CNIPA) on Apr. 21, 2022, the entire disclosures of which are incorporated by reference in their entirety herein.

TECHNICAL FIELD

The present disclosure relates to the technical field of clinical medical devices, and in particular, to an inner bushing and an ultrasonic endoscope.

BACKGROUND

Ultrasonic endoscopy is a digestive tract inspection technique that combines an endoscope and an ultrasound, where a miniature ultrasonic probe is mounted to the top end of the endoscope, and after the endoscope is inserted into the body cavity, the ultrasonic probe may be used to perform a real-time scan to obtain histological features of hierarchical structure of the gastrointestinal tract and ultrasonic images of surrounding adjacent organs while the endoscope is used to directly observe mucosal lesions of the digestive tract mucosapathy, so as to further improve the diagnosis level of the endoscope.

Since the size of the digestive tract of the human body is small, a high degree of precision is required in assembling the endoscope and the ultrasonic probe. In this disclosure, an alternative means of attachment with improved means of alignment of the attachment with the endoscope is described.

SUMMARY

The following summary is provided to facilitate an understanding of some of the innovative features unique to the aspects disclosed herein and is not intended to be a full description. A full appreciation of the various aspects can be gained by taking the entire specification, claims, and the abstract as a whole.

In various aspects, a sleeve configured to be dispositioned between an endoscope and an ultrasound accessory selectively attachable to the endoscope is disclosed. The sleeve can include a rigid body with an inner surface and an outer surface, wherein the rigid body is configured to maintain a structural integrity of the sleeve. The sleeve can further include a first flexible layer positioned about the inner surface of the rigid body and configured to create a friction fit between the inner surface of the rigid body and an outer surface of the endoscope. The sleeve can further include a second flexible layer positioned about the outer surface of the rigid body and configured to create a friction fit between the outer surface of the rigid body and the ultrasound accessory.

In various aspects, an inner bushing is disclosed. The inner bushing can include a sleeve and a positioning part connected at an end of the sleeve, wherein the sleeve is positioned around an outer side wall of a distal end of an endoscope, and an outer side wall of the sleeve is used for matching and connecting with a surgical attachment. The positioning part can be blocked at an end face of the distal end and the positioning part can be inserted into a channel of the endoscope, and the surgical attachment can be aligned and connected with the positioning part.

In various aspects, an assembly for an endoscope is disclosed. The assembly can include an ultrasonic probe and an inner bushing. The ultrasonic probe can include a probe body and an ultrasonic accessory positioned around the outer side wall of the sleeve. The probe body can be connected with the ultrasonic accessory.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF DRAWINGS

In order to more clearly illustrate the technical solutions in aspects of the present disclosure or the prior art, the following is a brief description of the accompanying drawings. Obviously, the accompanying drawings described below are some aspects of the present disclosure.

DETAILED DESCRIPTION

Endoscopic ultrasonography (EUS), is performed using an ultrasonic endoscope, a medical device that enables both ultrasound and endoscopic examinations to be performed using one device. After the endoscope enters into the body cavity, under the direct view of the endoscope, ultrasound tomographic imaging is performed on visceral organ walls or adjacent visceral organs, to obtain ultrasonic images of various layers below mucosae of visceral organ walls and of adjacent visceral organs, such as the mediastinum, pancreas, bile duct, lymph node, and the like. The ultrasonic endoscope has great advantages in staging gastrointestinal tumors and determining the nature of tumors of intestinal wall origin.

The ultrasonic endoscope may further use an ultrasound echo signal to generate an ultrasonic image, so as to guide fine needle aspiration biopsy in real-time as well as tumor injection therapy, pancreatic cyst puncture and drainage surgery, and the like.

When the ultrasonic endoscope is assembled, a miniature ultrasonic probe is mounted at one end of the endoscope inserted into the body cavity. After the endoscope is inserted into the body cavity, the digestive tract may be observed directly via the endoscope, and ultrasonic images of the gastrointestinal tract and adjacent visceral organs may be obtained by real-time scanning of the ultrasonic probe.

After the ultrasonic probe is assembled to an end portion of the endoscope, it is important to provide sufficient grip on to the endoscope to avoid movement of the ultrasound assembly during a procedure, as well as to provide necessary precision alignment with the working channel of the endoscope. Precision alignment is critical to align the working channel of the endoscope with the ultrasound scan plane, so that instrumentation inserted through the scope working channel is viewable in the ultrasound image.

In view of this, aspects of the present disclosure provide an inner bushing and an ultrasonic endoscope. The inner bushing is sleeved around an outer side wall of a distal end of the endoscope, a surgical attachment (e.g. ultrasonic probe) is sleeved around an outer side wall of the inner bushing. The inner bushing may increase a friction between the surgical attachment and the endoscope to ensure a secure assembly between the surgical attachment and the endoscope and allows a position of the surgical attachment to be precisely aligned during the assembly process, which not only ensures patient safety but also reduces operating time.

In order to make the objects, technical solutions, and advantages of the aspects of the present disclosure more clear, the technical solutions in the aspects of the present disclosure will be clearly and completely described below in combination with the accompanying drawings in the aspects of the present disclosure. Obviously, the described aspects are only part of the present disclosure.

Figure 1:
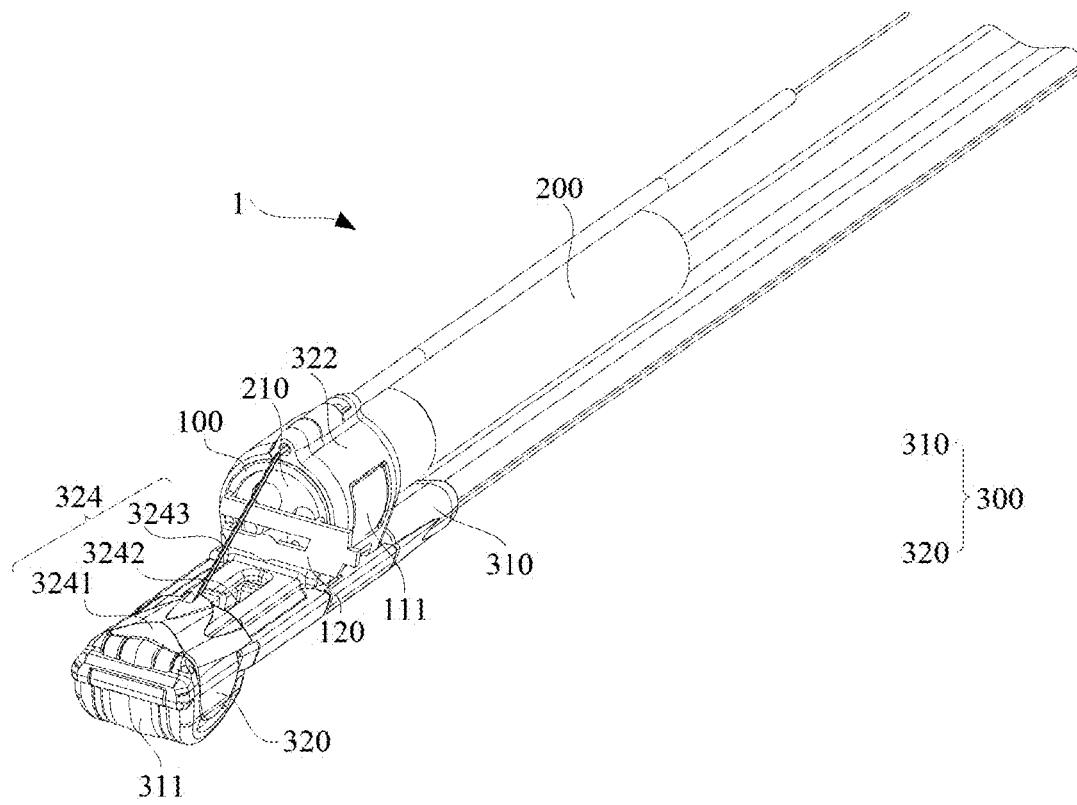
FIG. 1 illustrates a schematic structural diagram of an ultrasonic endoscope, according to at least one non-limiting aspect of the present disclosure.
Figure 2:
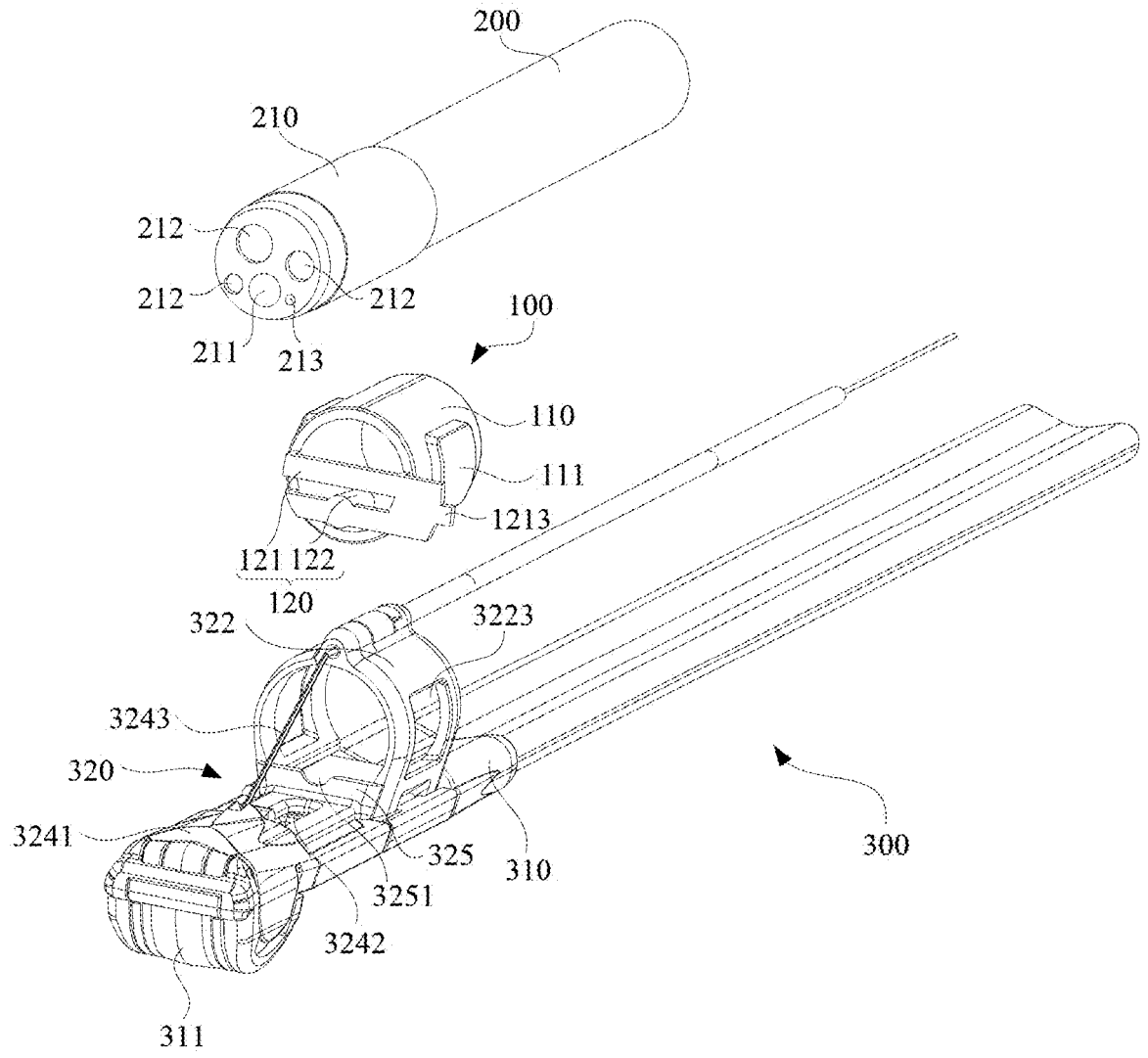
FIG. 2 illustrates an exploded view of FIG. 1, according to at least one non-limiting aspect of the present disclosure.
Figure 3:
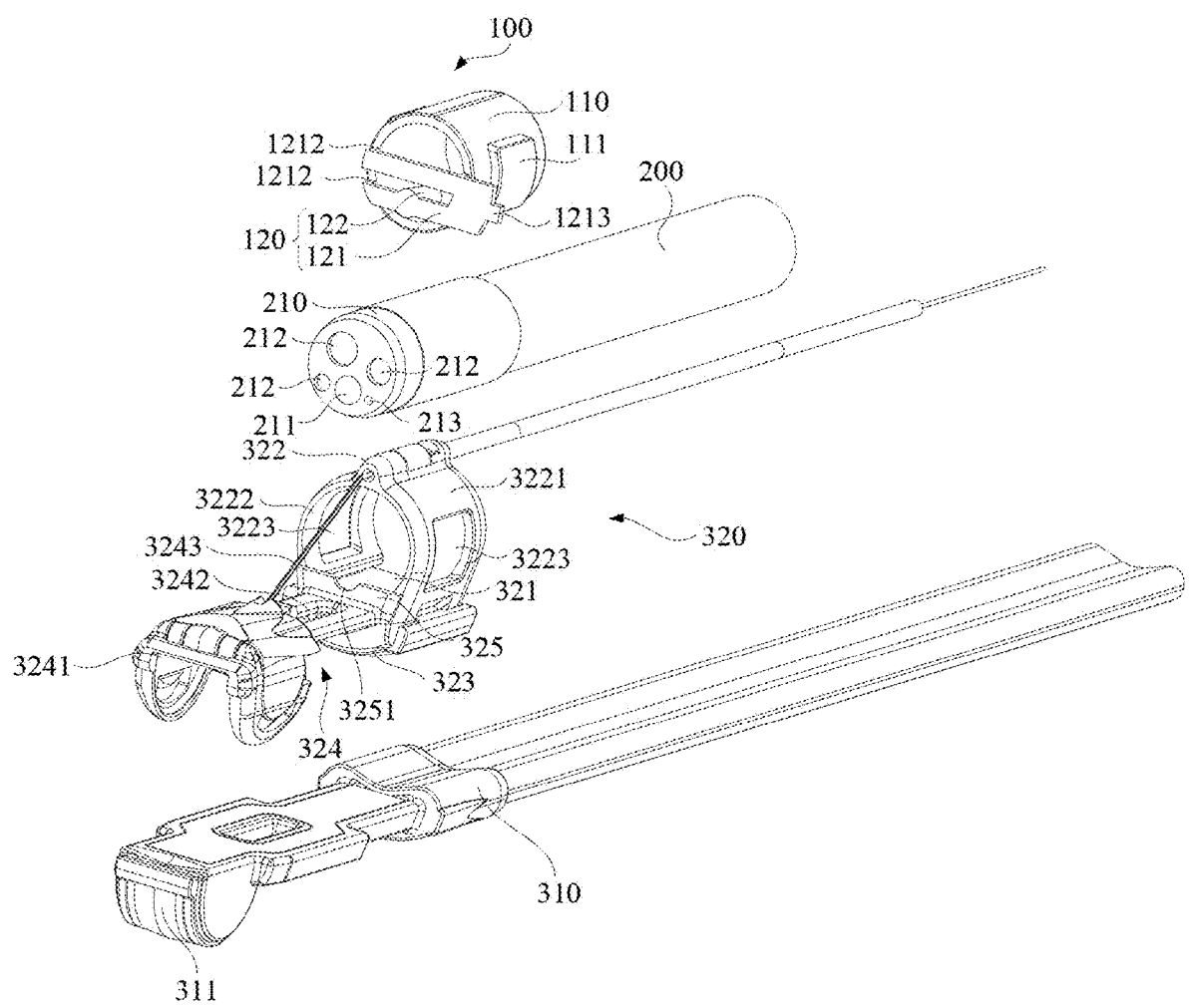
FIG. 3 illustrates a schematic structural diagram of an ultrasonic probe in FIG. 2 after disassembling, according to at least one non-limiting aspect of the present disclosure.
Figure 4:
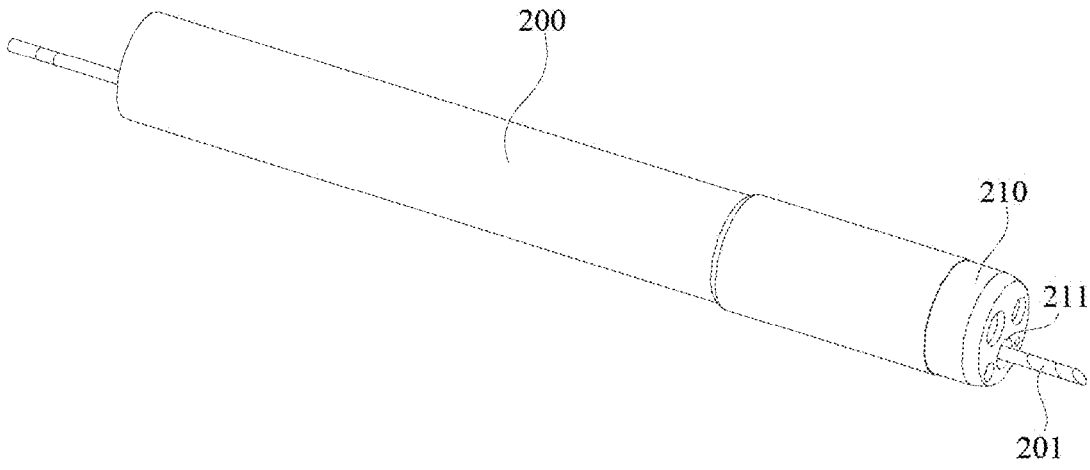
FIG. 4 illustrates a schematic diagram of an operation instrument inserted into an endoscope, according to at least one non-limiting aspect of the present disclosure.

FIG. 1 is a schematic structural diagram of an ultrasonic endoscope provided by an aspect of the present disclosure; FIG. 2 is an exploded view of FIG. 1; FIG. 3 is a schematic structural diagram of an ultrasonic probe in FIG. 2 after disassembling; FIG. 4 is a schematic diagram of an operation instrument inserted into an endoscope provided by an aspect of the present disclosure.

Referring to FIG. 1 to FIG. 3, the present aspect provides an ultrasonic endoscope 1, the ultrasonic endoscope 1 includes an endoscope 200, an ultrasonic probe 300 and an inner bushing 100.

The endoscope 200, which, according to some non-limiting aspects, can include a celoscope, can be configured as a tube with a micro camera, an illumination light source, and other mechanical structures. The endoscope 200 is, for example, a glass fiber tube. Two ends of the endoscope are defined as proximal end and distal end, respectively; the proximal end is an end closest to the operator, and the distal end is an end away from the operator. In order to facilitate illustration of the assembled structures of the ultrasonic endoscope 1, only part of a tube segment in which the endoscope 200 is inserted into the body cavity is shown in the figures An end of the endoscope 200 shown in the figures is a distal end 210 thereof.

Referring to FIG. 2, multiple light transmission holes are provided on an end face of the distal end 210 of the endoscope 200, and components, such as an illumination lamp and camera, are disposed corresponding to these light transmission holes 212, where light emitted by the illumination lamp passes through the light transmission holes 212 to illuminate the surrounding tissue environment, and the camera collects the surrounding images via the light. In addition, the end face of the distal end 210 of the endoscope 200 is further provided with other holes, such as, water injection hole 213 for liquid to flow. Furthermore, as shown in FIG. 4, a channel 211 is provided inside the endoscope 200, and the channel 211 is used for insertion of the operation instrument 201, such as a probe inserted into the channel 211.

Referring to FIG. 1 and FIG. 2, the ultrasonic probe 300 is installed at the distal end 210 of the endoscope 200, so that the endoscope 200 is used to directly observe mucosal lesions of the digestive tract. Meanwhile the ultrasonic probe 300 installed at the end of the endoscope 200 is used to perform real-time scanning, to obtain histological features of the hierarchical structure of the gastrointestinal tract and ultrasonic images of surrounding organs, thereby further improving diagnostic levels of the endoscope 200 and the ultrasound image.

Referring to FIG. 3, the ultrasonic probe 300 includes a probe body 310 and ultrasonic accessory 320. The ultrasonic probe 300 mainly achieves an ultrasonic scanning function via the probe body 310; ultrasonic accessory 320 is sleeved around the outer side wall of the distal end 210 of the endoscope 200 and is used to fix the probe body 310, and the ultrasonic accessory 320 cooperates with the probe body 310 to achieve function of the ultrasonic probe 300.

Exemplarily, the probe body 310 includes an acoustic lens 311 at an end thereof. The ultrasonic accessory 320 may include a supporting plate 321, a locking part 322, a splint 323, and a functional part 324. The supporting plate 321 is used as a basic support, the locking part 322 is connected at one side of the supporting plate 321, the splint 323 is connected at the other side of the supporting plate 321, the locking part 322 is sleeved around the outer side wall of the distal end 210 of the endoscope 200 to enable the ultrasonic accessory 320 to be assembled at the distal end 210 of the endoscope 200, a locking space is formed between the splint 323 and the supporting plate 321, and the probe body 310 is locked between the splint 323 and the supporting plate 321 so as to fix the probe body 310 via the ultrasonic accessory 320.

The functional part 324 is connected at the front end of the supporting plate 321, and the functional part 324 and the probe body 310 jointly achieve the function of the ultrasonic probe 300. Exemplarily, as shown in FIG. 3, the functional part 324 may include an electronic part 3241 at the front end of the ultrasonic accessory 320 and an ultrasonic channel 3242 between the supporting plate 321 and the electronic part 3241, where the electronic part 3241 is connected with a conductive wire 3243.

Referring to FIG. 1 to FIG. 3, in the present aspect, in order to make the ultrasonic accessory 320 securely sleeved around the outer side wall of the distal end 210 of the endoscope 200, the inner bushing 100 is sleeved around the outer side wall of the distal end 210 of the endoscope 200, and the locking part 322 of the ultrasonic accessory 320 is sleeved around the outer side wall of the inner bushing 100.

The inner bushing 100 will be illustrated in detail in conjunction with the endoscope 200 and the ultrasonic probe 300. It should be noted that the present aspect will be illustrated by an example where the surgical attachment assembled at the distal end 210 of the endoscope 200 is the ultrasonic probe 300. In a practical application, other surgical attachments may be assembled at the distal end 210 of the endoscope 200, and similarly, sleeving the inner bushing 100 on the outer side wall of the endoscope 200 may increase friction between the operation attachment and the endoscope 200, such that the surgical attachment can be assembled firmly and the surgical attachment can be positioned via the inner bushing 100.

Figure 5:
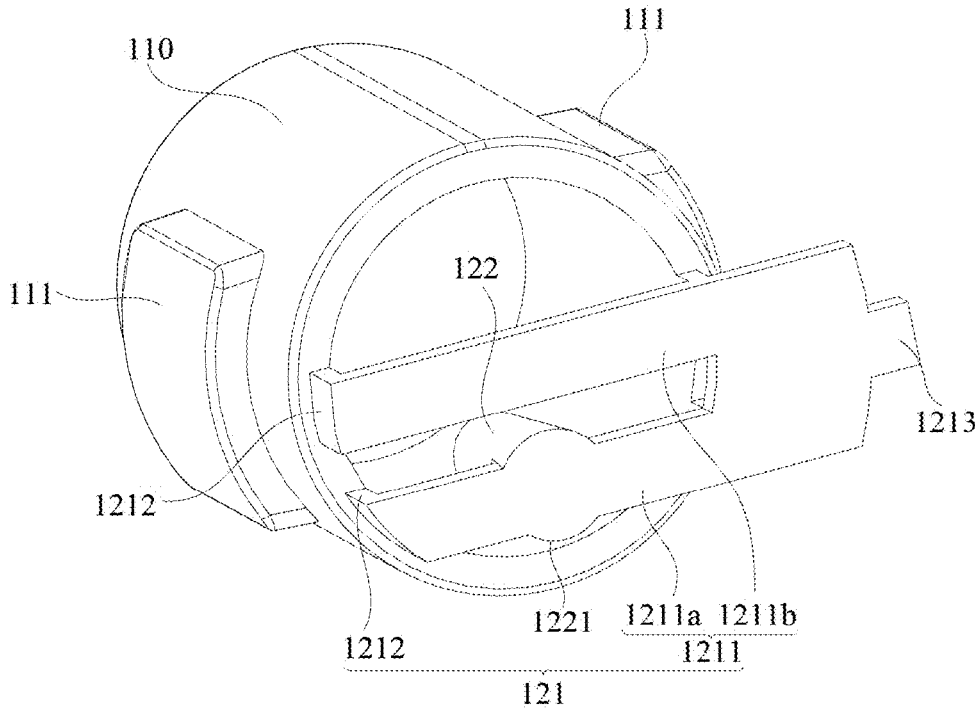
FIG. 5 illustrates a schematic structural diagram of an inner bushing, according to at least one non-limiting aspect of the present disclosure.
Figure 6:
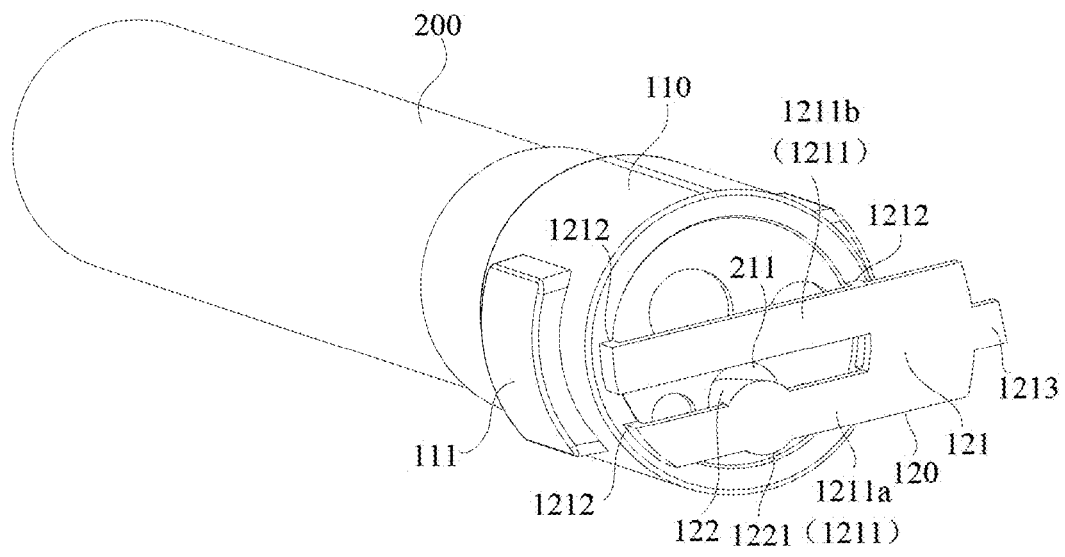
FIG. 6 illustrates a schematic structural diagram of an inner bushing assembled to the endoscope, according to at least one non-limiting aspect of the present disclosure.
Figure 7:
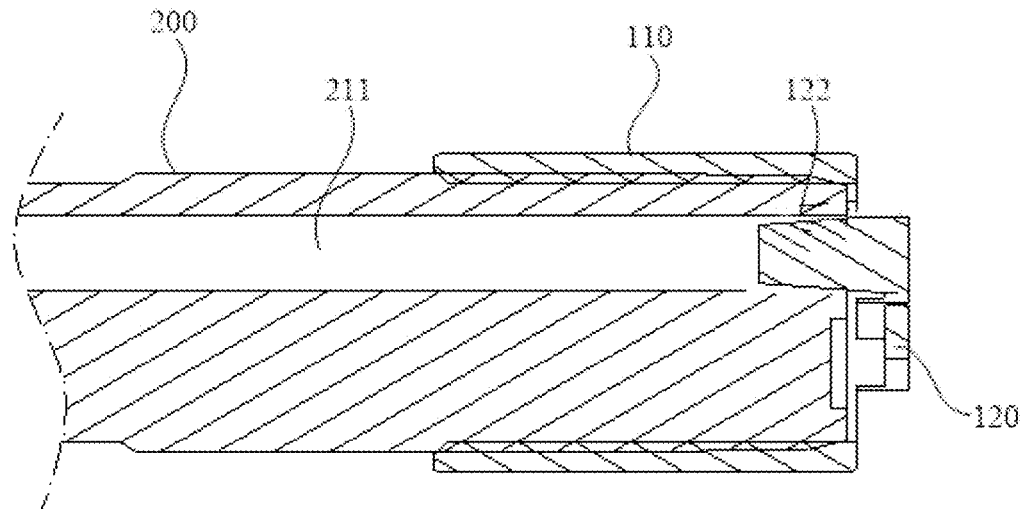
FIG. 7 illustrates a sectional view of FIG. 6, according to at least one non-limiting aspect of the present disclosure.
Figure 8:
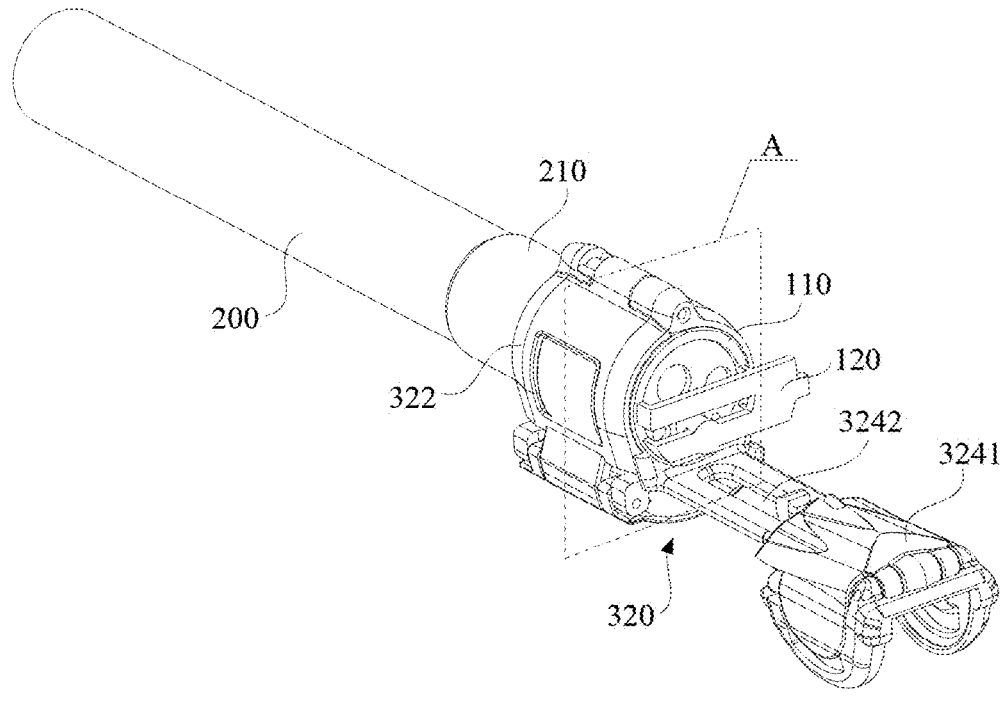
FIG. 8 illustrates a schematic structural diagram of an ultrasonic accessory assembled to an endoscope, according to at least one non-limiting aspect of the present disclosure.
Figure 9:
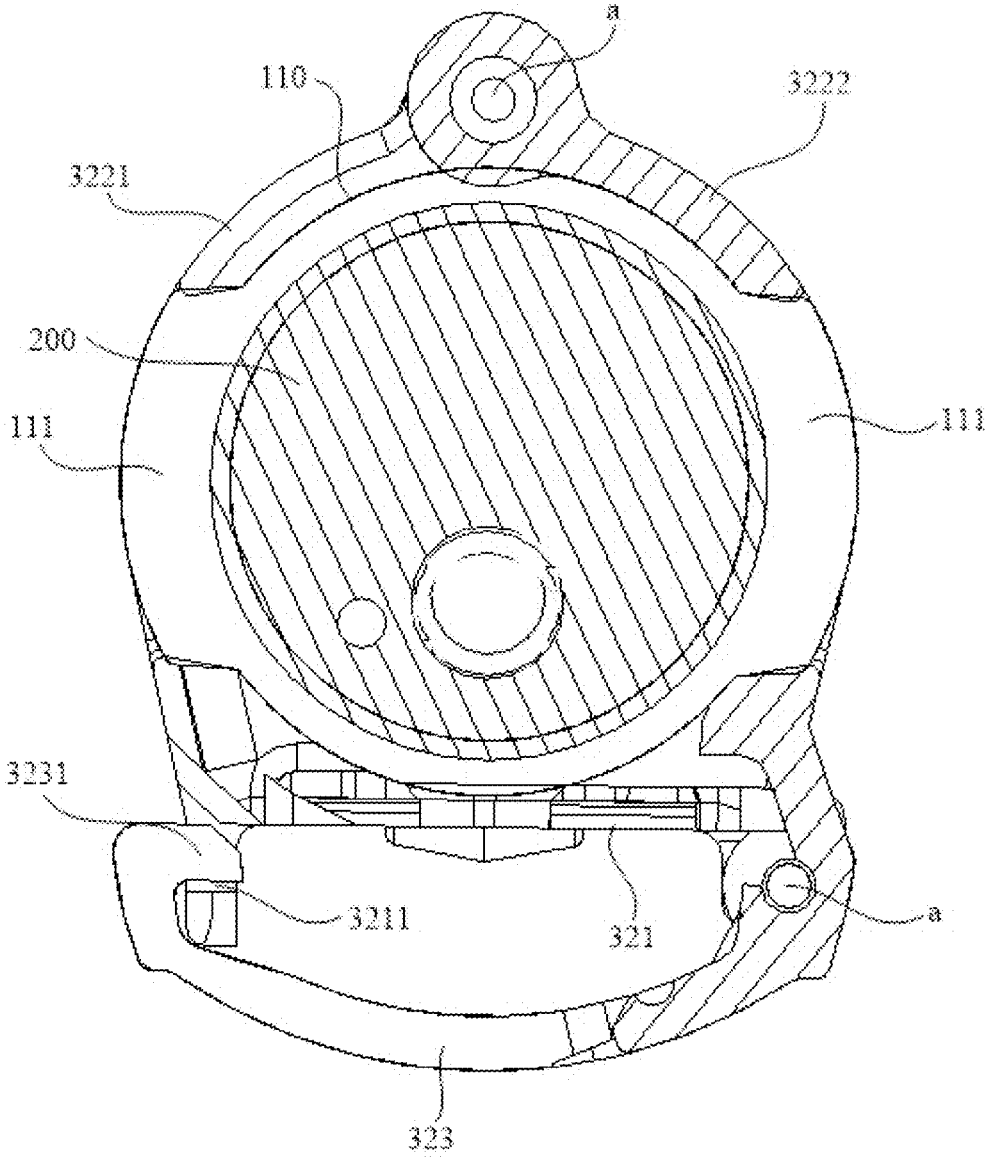
FIG. 9 illustrates a schematic cross-sectional view at A in FIG. 8, according to at least one non-limiting aspect of the present disclosure.

FIG. 5 is a schematic structural diagram of an inner bushing provided by an aspect of the present disclosure; FIG. 6 is a schematic structural diagram of an inner bushing assembled to an endoscope; FIG. 7 is a sectional view of FIG. 6; FIG. 8 is a schematic structural diagram of an ultrasonic accessory assembled to an endoscope provided by an aspect of the present disclosure; and FIG. 9 is a schematic cross-sectional view at A in FIG. 8.

Referring to FIG. 5, the inner bushing 100 includes a sleeve 110 and a positioning part 120, and the sleeve 110 may be a flexible sleeve. As shown in FIG. 1, the sleeve 110 is sleeved around the outer side wall of the endoscope 200, the locking part 322 of the ultrasonic accessory 320 is sleeved around the outer side wall of the sleeve 110, and the friction between the sleeve 110 and the outer side wall of the endoscope 200 and the friction between the sleeve 110 and the locking part 322 of the ultrasonic accessory 320 are large, which may ensure a firm installation of the ultrasonic accessory 320. Even when the doctor operates the ultrasonic endoscope 1, the ultrasonic probe 300 is in contact with an inner wall of the body cavity, there is no deviation between the ultrasonic accessory 320 and the endoscope 200, and the doctor's operation process will not be affected, and the safety of the operation may be effectively guaranteed.

Moreover, there is a flexible contact between the flexible sleeve 110 and the outer side wall of the endoscope 200. Compared with a rigid ultrasonic accessory 320 that is sleeved directly on the outer side wall of the endoscope 200, by providing an additional sleeve 110 i on the outer side wall of the endoscope 200, the damage to the endoscope 200 can be significantly reduced by the cushioning effect of the sleeve 110, decreasing the probability of damage to the endoscope 200 during assembly and increasing the service life of the endoscope 200.

Referring to FIG. 6, the positioning part 120 is connected at an end of the sleeve 110, and the positioning part 120 is located at an end of the sleeve 110 corresponding to an end face of the distal end 210 of the endoscope 200 and is blocked at the end face of the endoscope 200. An orientation of the sleeve 110 may be positioned via the positioning part 120, then the ultrasonic accessory 320 may be positioned through alignment and assembly between the positioning part 120 and the ultrasonic accessory 320.

Specifically, as shown in conjunction with FIG. 5 and FIG. 6, the positioning part 120 of the inner bushing 100 may include a connecting plate 121 and a positioning post 122. The connecting plate 121 is connected at an end face of the sleeve 110, and the connecting plate 121 spans both sides of the sleeve 110, extending from one side of the sleeve 110 to the other side of the sleeve 110. The positioning post 122 is connected to the connecting plate 121. Where the positioning post 122 is connected to a surface of a side of the connecting plate 121 facing the sleeve 110, that is, the positioning post 122 is disposed on a surface of a side of the connecting plate 121 facing the endoscope 200 with an end of the positioning post 122 connecting to the connecting plate 121 being a connecting end thereof and an end opposite to the connecting end being a free end, taking this as an example, the free end of the positioning post 122 extends into the endoscope 200.

Referring to FIG. 7, when installing the inner bushing 100, the positioning post 122 of the positioning part 120 of the inner bushing 100 directly faces channel 211 of the endoscope 200, which enables the free end of the positioning post 122 to be inserted into the channel 211 of the endoscope 200. Thereby, the inner bushing 100 may be positioned; then, when the ultrasonic probe 300 is sleeved subsequently on the outside of the inner bushing 100, the ultrasonic probe 300 may be positioned.

Where referring to FIG. 3, the locking part 322 of the ultrasonic accessory 320 is connected with a positioning plate 325. The positioning plate 325 is disposed at a side of the locking part 322 corresponding to the end face of the distal end 210 of the endoscope 200, and the positioning plate 325 cooperates with the connecting plate 121 of the inner bushing 100 to position the ultrasonic accessory 320. Referring to FIG. 1, when the ultrasonic accessory 320 is sleeved outside the inner bushing 100, the positioning plate 325 of the locking part 322 of the ultrasonic accessory 320 is in alignment with and in contact with the connecting plate 121 of the positioning part 120 of the inner bushing 100, thereby positioning the ultrasonic accessory 320.

Exemplarily, in accordance with a position of the channel 211 of the endoscope 200, such as when the channel 211 is provided close to a center of the endoscope 200, or the channel 211 is provided eccentrically and close to an edge of the endoscope 200, the connecting plate 121 of the inner bushing 100 is provided corresponding to the channel 211 of the endoscope 200, and the positioning plate 325 that is in alignment with and in contact with the connecting plate 121 may be provided close to the supporting plate 321 of the ultrasonic accessory 320. There is a spacing between the positioning plate 325 and the supporting plate 321, or the positioning plate 325 extends to connect with the supporting plate 321.

Referring to FIG. 5, in the present aspect, in order to position precisely the ultrasonic accessory 320, a diameter of the positioning post 122 may be greater than a width of an area on the connecting plate 121 corresponding to a connecting part of the positioning post 122. A portion of the connecting end of the positioning post 122 is exposed outside the connecting plate 121. The portion of the connecting end of the positioning post 122 located outside the connecting plate 121 forms a positioning protrusion 1221. The positioning protrusion 1221 protrudes toward the positioning plate 325 of the ultrasonic accessory 320.

Referring to FIG. 3, corresponding to the positioning protrusion 1221 of the positioning post 122 of the inner bushing 100, the positioning plate 325 of the ultrasonic accessory 320 is provided with a positioning notch 3251. The positioning notch 3251 is matched with the positioning protrusion 1221 in shape and size. When the ultrasonic accessory 320 is sleeved outside the inner bushing 100, the positioning notch 3251 on the positioning plate 325 of the ultrasonic accessory 320 corresponds to the positioning protrusion 1221 of the positioning post 122 of the inner bushing 100. The positioning protrusion 1221 of the positioning post 122 extends into the positioning notch 3251 of the positioning plate 325 to position the ultrasonic accessory 320.

In a practical application, after assembling the ultrasonic endoscope 1, the positioning post 122 of the positioning part 120 of the inner bushing 100 needs to be moved out of the channel 211 of the endoscope 200 so as to expose an opening of the channel. Since the positioning plate 325 of the ultrasonic accessory 320 is aligned with and in contact with the connecting plate 121 of the inner bushing 100, the positioning plate 325 of the ultrasonic accessory 320 does not block the opening of the channel of the endoscope 200. In this way, the operation instrument 201 may be inserted into the channel 211 of the endoscope 200, and the operation instrument 201 passes through the opening of the channel and extends out of the endoscope 200.

In the present aspect, the inner bushing 100 may be sleeved around the outer side wall of the endoscope 200 by a force in the form of interference connection, and by the pressure and the friction there between, the inner bushing 100 is fixed onto the outer side wall of the endoscope 200. Alternatively, the inner bushing 100 and the endoscope 200 can be fixedly connected to each other by the means of snap-fit, screw locking, or adhesive. The present aspect has no specific limitation in this regard.

In addition, in some aspects, the sleeve 110 of the inner bushing 100 may be an integrally formed flexible sleeve, such as a silicone sleeve or a rubber sleeve, or the sleeve 110 may adopt a thin layer having certain deformation ability as an outer casing, the outer casing being internally filled with gas or liquid. The flexible sleeve has significant compliance, and there is a large friction force between the flexible sleeve and the endoscope 200 and between the flexible sleeve and the ultrasonic probe 300. The sleeve 110 of the inner bushing 100 enables firm connection and precise positioning between the endoscope 200 and the ultrasonic probe 300.

Where the inner bushing 100 as a whole may be an integrally formed piece, that is, the positioning part 120 may be integrally formed at an end face of the sleeve 110, the positioning part 120 may be made of a silicone material or a rubber material. Alternatively, the inner bushing 100 as a whole may adopt a thin layer having certain deformation ability as an outer casing, the outer casing being internally filled with gas or liquid. Alternatively, when manufacturing the inner bushing 100, the positioning part 120 may also be formed separately, such as the positioning part 120 may be fixedly connected with the end face of the sleeve 110 by the means of snap-fit, screw locking, or adhesive.

In other aspects, the sleeve 110 of the inner bushing 100 may be composed of a rigid body and a flexible layer attached to inner and outer side walls of the body, such as, the body of the sleeve 110 being a metal cylinder or a hard plastic cylinder and the inner and outer side walls of the metal cylinder or the hard plastic cylinder being attached with a flexible rubber layer or silicone layer. In this way, the rigidity of the sleeve 110 can be improved, and there is a large friction between the sleeve 110 and the endoscope 200 and between the sleeve 110 and the ultrasonic probe 300 so as to ensure the firm connection of the ultrasonic probe 300.

The positioning part 120 may be made of the same material as the flexible layer of the sleeve 110. For example, the positioning part 120 may be made of a silicone material or a rubber material, or the positioning part 120 may be a structure in which the flexible outer casing is internally filled with gas or liquid. Exemplarily, the positioning part 120 may be integrally formed with the flexible layer of the sleeve 110, or the positioning part 120 may be fixedly connected with an end face of the sleeve 110 by the means of snap-fit, screw lock, or adhesive.

Referring to FIG. 5, for the case where the positioning part 120 is integrally formed with the sleeve 110, the connecting plate 121 of the positioning part 120 may include a plate part 1211 and connecting feet 1212, the plate part 1211 extending along an end face of the sleeve 110 from one side to another side of the sleeve 110, spanning both sides of the end of the sleeve 110, and the connecting feet 1212 connecting at positions of the plate part 1211 corresponding to two sides of the end face of the sleeve 110. The connection between the plate part 1211 and the end face of the sleeve 110 may be achieved via the connecting feet 1212.

In this way, the connecting feet 1212 and the plate part 1211 have different extending directions. For example, the connecting feet 1212 are vertical to the plate part 1211, and a gap between the plate part 1211 and the sleeve 110 is small and the size of the connecting feet 1212 is small, to facilitate separation of the positioning part 120 from the sleeve 110. Application of a small external force may rip out the connecting feet 1212 and separate the connecting plate 121 from the sleeve 110, thereby allowing the positioning post 122 to be released from the channel 211 of the endoscope 200.

Continuing to refer to FIG. 5, due to the small overall size of the inner bushing 100, in order to ensure sufficient strength of the positioning part 120 connected at the end of the sleeve 110, the plate part 1211 may include a main body part 1211a and a reinforcement part 1211b. The positioning post 122 is connected to the main body part 1211a, which serves as a connection base of the positioning post 122. In the width direction of the plate part 1211, the reinforcement part 1211b is located at one side of the main body part 1211a. Providing the reinforcement part 1211b may increase the width of the plate part 1211 and enhance the strength of the plate part 1211, avoiding a phenomenon that the connection between the positioning part 120 and the end of the sleeve 110 is not firm during the manufacturing process.

When assembling the ultrasonic accessory 320, the positioning plate 325 of the ultrasonic accessory 320 is aligned with and in contact with the main body part 1211a of the positioning part 120 of the inner bushing 100. Regarding the positioning post 122 connected to the main body part 1211a, one side of the positioning post 122 away from the reinforcement part 1211b is located out of the main body part 1211a to form a positioning protrusion 1221, so as to cooperate with the positioning notch 3251 of the positioning plate 325 of the ultrasonic accessory 320.

In the width direction of the positioning part 120, the reinforcement part 1211b may extend in a direction away from the main body part 1211a from one side of the main body part 1211*a.* There is no gap between the reinforcement part 1211*b* and the main body part 1211*a,* which is equivalent so that the positioning post 122 is disposed eccentrically and close to one side of the plate part 1211. Alternatively, as shown in FIG. 5, there is a gap between the reinforcement part 1211*b* and the main body part 1211*a,* and exemplarily, part of an area of the connecting end of the positioning post 122 may be exposed within the gap between the main body part 1211*a* and the reinforcement part 1211*b;* that is, two sides of the connecting end of the positioning post 122 are both disposed out of the main body part 1211*a.* In this way, it is convenient to observe the positioning post 122 from the gap between the main body part 1211*a* and the reinforcement part 1211*b,* which is helpful in aligning the positioning post 122 with the channel 211 of the endoscope 200 and quickly and accurately inserting the positioning post 122 into the channel 211 of the endoscope 200.

In addition, the main body part 1211*a* and the reinforcement part 1211*b* are both connected with a connecting foot 1212. The main body part 1211*a* and the reinforcement part 1211*b* are each connected with the sleeve 110 via respective connecting feet 1212. The connecting feet 1212 extend from the main body part 1211*a* to the reinforcement part 1211*b* to avoid a too-long extension length of the connecting foot 1212. The size of the connecting feet 1212 is maintained to be small to ensure that the connecting feet 1212 are easily pulled apart.

In order to facilitate the pulling apart of the connecting plate 121 of the inner bushing 100, as shown in FIG. 5, one side of the connecting plate 121 may extend to protrude from a side of the sleeve 110. The part of the connecting plate 121 protruding out of the sleeve 110 forms an easy-pull end 1213, and the easy-pull end 1213 forms a force application portion. The operator may apply a force to the connecting plate 121 by holding the easy-pull end 1213 of the connecting plate 121, thereby pulling apart the connecting plate 121 from the end of the sleeve 110.

Alternatively, both sides of the connecting plate 121 may extend to protrude from a side of the sleeve 110, and both sides of the connecting plate 121 may be used as easy-pull ends 1213. This makes it convenient for the user to operate without the need to identify on which side the easy-pull end 1213 of the connecting plate 121 is located, which may improve the operation efficiency.

In an practical application, it is possible to pull apart the positioned feet 1212 connected at two sides of the connecting plate 121. The connecting plate 121 as a whole is separated from the end of the sleeve 110, and the connecting plate 121 is completely separated from the sleeve 110. It is also possible to pull apart only the connecting foot 1212 located at one side of the easy-pull end 1213. One end of the connecting plate 121 is separated from the sleeve 110, and the other end of the connecting plate 121 is still connected with the sleeve 110. It is sufficient that the connecting plate 121 does not affect the operation of the endoscope 200 by twisting the connecting plate 121 to an angle that does not block the end face of the endoscope 200.

In addition, referring to FIG. 4, in the present aspect, the inner bushing 100 and the ultrasonic accessory 320 of the ultrasonic probe 300 may be manufactured separately. T the ultrasonic accessory 320 is then assembled to the outer side wall of the inner bushing 100. Alternatively, in other aspects, the inner bushing 100 and the ultrasonic accessory 320 may be an integrally formed piece. In this case, for the ultrasonic accessory 320 with a strength requirement, since the inner bushing 100 is a flexible member, exemplarily, the inner bushing 100 can be injected to an inner side of the locking part 322 of the ultrasonic accessory 320 by a two-material injection molding process.

In order to better observe the tissue environment around the ultrasonic endoscope 1 and the state inside the endoscope 200, for example, an insertion state of the operation instrument 201 in the channel 211 of the endoscope 200, in the present aspect, the endoscope 200, the inner bushing 100, and the ultrasonic probe 300 may be made of a highly transparent material so that a medical staff can cleanly observe the state of the internal structure of the ultrasonic endoscope 1.

As shown in conjunction with FIG. 3, FIG. 8, and FIG. 9, for the case in which the ultrasonic accessory 320 is assembled to the outer wall of the inner bushing 100, the locking part 322 of the ultrasonic accessory 320 may be locked to the outer side wall of the sleeve 110 of the inner bushing 100, where the locking part 322 of the ultrasonic accessory 320 may include a first locking plate 3221 and a second locking plate 3222. The first locking plate 3221 may be fixedly connected with one side of the supporting plate 321, one side of the second locking plate 3222 being connected rotatably with the first locking plate 3221 and the other side of the second locking plate 3222 being locked to the other side of the supporting plate 321.

Exemplarily, the first locking plate 3221 may be connected with the second locking plate 3222 by a rotation shaft a, and an openable and closable structure may be formed between the first locking plate 3221 and the second locking plate 3222. When installing the ultrasonic accessory 320, the second locking plate 3222 is first left unconnected to the supporting plate 321. The second locking plate 3222 is then opened, the locking part 322 is sleeved around the outer side wall of the inner bushing 100, and the second locking plate 3222 is then rotated and locked to the supporting plate 321.

It should be noted that when the second locking plate 3222 is locked to the supporting plate 321, an inner diameter of the locking part 322 may be slightly smaller than an outer diameter of the sleeve 110 of the inner bushing 100, such that an interference fit is used between the locking part 322 and the sleeve 110 to generate a pressing force on the sleeve 110, thereby firmly locking the ultrasonic accessory 320 to the outer side wall of the inner bushing 100.

In addition, as shown in conjunction with FIG. 3 and FIG. 9, as for the assembly of the probe body 310 and the ultrasonic accessory 320, exemplarily, one side of the splint 323 of the ultrasonic accessory 320 is connected rotatably with one side of the supporting plate 321. For example, one side of the splint 323 is connected rotatably with one side of the supporting plate 321 by the rotation shaft a, the other side of the splint 323 has a locking buckle 3231, and the other side of the supporting plate 321 has a locking hole 3211. When the splint 323 is rotated to a closed state, the locking buckle 3231 of the splint 323 is locked into the locking hole 3211 of the supporting plate 321 so as to lock the probe body 310 into the space between the splint 323 and the supporting plate 321.

As shown in FIG. 9, one side of the supporting plate 321 connected rotatably with the splint 323 may be the side of the supporting plate 321 locked to the second locking plate 3222 of the locking part 322. In this case, the splint 323 can be provided with an avoidance area, and the second locking plate 3222 of the locking part 322 may be locked into the avoidance area of the splint 323. Moreover, one side of the supporting plate 321 provided with the locking hole 3211 may be the side of the supporting plate 321 connected fixedly with the first locking plate 3221.

When assembling the probe body 310 and the ultrasonic accessory 320, the splint 323 is first made to be in an open state, the probe body 310 is assembled into the space between the splint 323 and the supporting plate 321. The splint 323 is then rotated to lock the locking buckle 3231 on the splint 323 into the locking hole 3211 of the supporting plate 321, and thus the probe body 310 is assembled to the ultrasonic accessory 320.

As shown in conjunction with FIG. 6 and FIG. 9, in order to position precisely the ultrasonic accessory 320, in the present aspect, the outer side wall of the sleeve 110 is further provided with a limiting boss 111, and the locking part 322 of the ultrasonic accessory 320 is provided with a limiting notch 3223. When assembling the ultrasonic accessory 320, the limiting notch 3223 on the locking part 322 corresponds to the limiting boss 111 on the outer side wall of the sleeve 110, and the limiting boss is locked into the limiting notch 3223 to position the ultrasonic accessory 320.

In this way, the positioning accuracy of the ultrasonic accessory 320 can be improved by matching positioning between the positioning plate 325 of the ultrasonic accessory 320 and the positioning part 123 of the inner bushing 100, along with the positioning between the limiting boss 111 of the inner bushing 100 and the limiting notch 3223 of the ultrasonic accessory 320. Moreover, when installing the ultrasonic accessory 320, the position alignment and contact between the positioning plate 325 of the ultrasonic accessory 320 and the positioning part 120 of the inner bushing 100 is achieved by locking the inner edge of the limiting notch 3223 of the locking part 322 to the outer edge of the limiting boss 111 of the inner bushing 100.

When installing the ultrasonic accessory 320, since the first locking plate 3221 of the locking part 322 is first locked to the outer side wall of the sleeve 110 of the inner bushing 100 and then the second locking plate 3222 is rotated to lock with the supporting plate 321, it is possible to provide the limiting notch 3223 on the first locking plate 3221 and provide the limiting boss 111 on the outer side wall of the sleeve 110 corresponding to the limiting notch 3223 of the first locking plate 3221.

Alternatively, in order to improve the positioning accuracy, both the first locking plate 3221 and the second locking plate 3222 are provided with a limiting notch 3223. The limiting notches 3223 on the first locking plate 3221 and the second locking plate 3222 may be disposed opposite to each other. Two opposite sides on the outer side wall of the sleeve 110 are each provided with a limiting boss 111. The limiting bosses 111 of the two sides are locked into the limiting notches 3223 of the first locking plate 3221 and the second locking plate 3222, respectively.

It should be understood that the words indicating orientation involved in the aspects, such as up, low, above, below, upper, lower, top, bottom, top end, bottom end, top end face, and bottom end face, are based on the position relationship in an installed and use state of the apparatus or the device.

In the present description, each aspect or implementation is described in a progressive manner. Each aspect focuses on the differences from other aspects, and the same and similar parts between the aspects can be referred to each other.

Finally, it should be noted that the above aspects are only used to illustrate the technical solutions of the present disclosure, not to limit it. Although the present disclosure has been described in detail with reference to the above aspects, those skilled in the art should understand that they can still modify the technical solutions recorded in the above aspects or equivalently replace some or all of the technical features therein; these modifications or replacements do not make the essence of the corresponding technical solutions deviate from the scope of the technical solutions of the aspects of the present disclosure.

Figure 10:
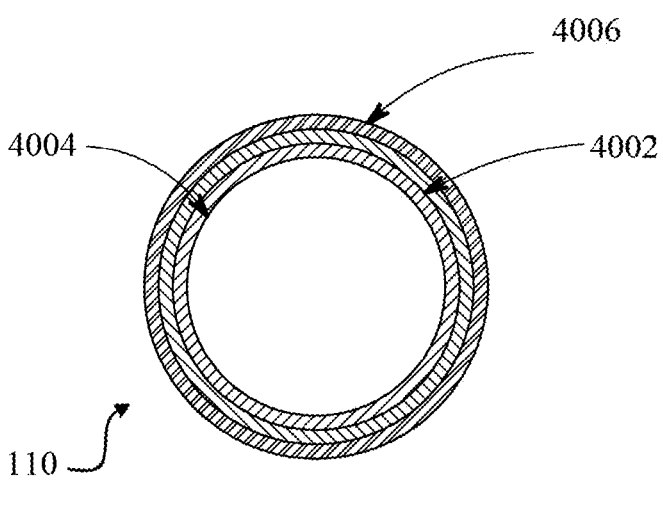
FIG. 10 illustrates a cross-sectional view of a sleeve of the inner bushing of the ultrasound accessory of FIG. 8, according to one non-limiting aspect of the present disclosure.

Referring now to FIG. 10, a cross-sectional view of the sleeve 110 of the inner bushing 100 (FIG. 3) of the ultrasound accessory 320 of FIG. 8 is depicted in accordance with at least one non-limiting aspect of the present disclosure. According to the non-limiting aspect of FIG. 10, the sleeve 110 of the inner bushing 100 (FIG. 3) can be cylindrically configured such that it can slide onto the front side of the endoscope 100 (FIG. 3). The sleeve 110 of the inner bushing 100 (FIG. 3) can further include a rigid body 4002 with a first flexible layer 4004 coupled to an inner surface of the rigid body 4002, and a second flexible layer 4006 coupled to an outer surface of the rigid body 4002. The rigid body 4002 of the sleeve 110 can be configured as a cylinder made of a harder material relative to the first flexible layer 4004 and the second flexible layer 4006. For example, the rigid body 4002 of the sleeve 110 can include a metal, a plastic, or a composite, amongst other relatively hard materials. The first flexible layer 4004 and the second flexible layer 4006 respectively coupled to the inner surface of the rigid body 4002, for example, can include a more flexible material, such as a rubber or a silicone, amongst other relatively soft materials. The first flexible layer 4004, the second flexible layer 4006, and the rigid body 4002 can be independently formed and coupled (e.g., via adhesive, fastener, weld, melt, etc.) from different materials or integrally formed from a single material, assuming the first flexible layer 4004, the second flexible layer 4006, and the rigid body 4002 remain portions of the single material with the aforementioned material properties. Accordingly, the rigid body 4002 can maintain the structural rigidity of the sleeve 110, while the first flexible layer 4004 and the second flexible layer 4006 ensure a proper friction fit between the sleeve 110, the endoscope 200 (FIG. 8), and the ultrasonic probe 300 (FIG. 2). The rigidity of the rigid body 4002 can enable the inner bushing 100 (FIG. 3) to be easily applied to the endoscope 100 (FIG. 3) from the front. Thus, it shall be appreciated that the sleeve 110 of the inner bushing 100 (FIG. 3) of the ultrasound accessory 320 (FIG. 8) is particularly and structurally configured to easily and firmly connect the ultrasound accessory 320 (FIG. 8) to the endoscope 200 (FIG. 8).

However, it shall be further appreciated that, according to other non-limiting aspects, either the first flexible layer 4004 or the second flexible layer 4006 can be omitted from the sleeve 110 of the inner bushing 100 (FIG. 3), as desired. According to some non-limiting aspects, the first flexible layer 4004 can be omitted and the inner surface of the rigid body 4002 can be configured for the desired fit about the endoscope 200 (FIG. 8). For example, a diameter of the inner surface of the rigid body 4002 can be configured for the desired fit about the endoscope 200 (FIG. 8). Alternately or additionally, a hardness of the inner surface of the rigid body 4002 can be less than that of the rest of the rigid body 4002, such that the rest of the rigid body 4002 can maintain the structural rigidity of the sleeve 110 while the inner surface of the rigid body 4002 can ensure a proper friction fit between the sleeve 110 and the endoscope 200 (FIG. 8). Likewise, according to other non-limiting aspects, the second flexible layer 4006 can be omitted and the outer surface of the rigid body 4002 can be configured for the desired fit relative to the ultrasound accessory 320 (FIG. 8). For example, a diameter of the outer surface of the rigid body 4002 can be configured for the desired fit about the ultrasound accessory 320 (FIG. 8).

Alternately or additionally, according to other non-limiting aspects, a hardness of the outer surface of the rigid body 4002 can be less than that of the rest of the rigid body 4002, such that the rest of the rigid body 4002 can maintain the structural rigidity of the sleeve 110 while the outer surface of the rigid body 4002 can ensure a proper friction fit between the sleeve 110 and the ultrasound accessory 320 (FIG. 8). As previously described, according to still other non-limiting aspects, the first flexible layer 4004, the second flexible layer 4006, and the rigid body 4002 can be integrally formed from a single material, assuming the first flexible layer 4004, the second flexible layer 4006, and the rigid body 4002 remain portions of the single material with the aforementioned material properties. As such, the dimensions of the first flexible layer 4004, the second flexible layer 4006, and the rigid body 4002 can be particularly configured to ensure the desired fit.

Specifically, the first flexible layer 4004 and the second flexible layer 4006 of the sleeve 110 of FIG. 10 can be installed adjacent to an inner side of a locking part 322 (FIG. 8) of the ultrasound accessory 320 (FIG. 8). Although, as previously described, the inner bushing 100 (FIG. 3) can be injected into the inner side of the locking part 322 (FIG. 8), according to other non-limiting aspects, the inner bushing 100 (FIG. 3) can be manufactured prior to installation and otherwise installed into the locking part 322 (FIG. 8) of the ultrasound accessory 320 (FIG. 8) via an adhesive, a friction fit, or mechanical coupling. According to other non-limiting aspects, the inner bushing 100 (FIG. 3) can be co-molded to the inner part of any rigid plastic parts that interface the endoscope, including the supporting plate 321 (FIG. 8), such that the inner bushing 100 (FIG. 3) is integral to the locking part 322 (FIG. 8) of the ultrasound accessory 320 (FIG. 8). The inner bushing 100 (FIG. 3) may also be co-molded to the inner part of any rigid plastic parts that interface with the endoscope. This may include the supporting plate 321 (FIG. 3). Additionally, the inner part of positioning plate 325 (FIG. 3) may be co-molded with the inner bushing 100 (FIG. 3) to increase a friction force created between the front face of the endoscope 200 (FIG. 3) and to provide protection to the front face of the endoscope 200 (FIG. 3).

Figure 11:
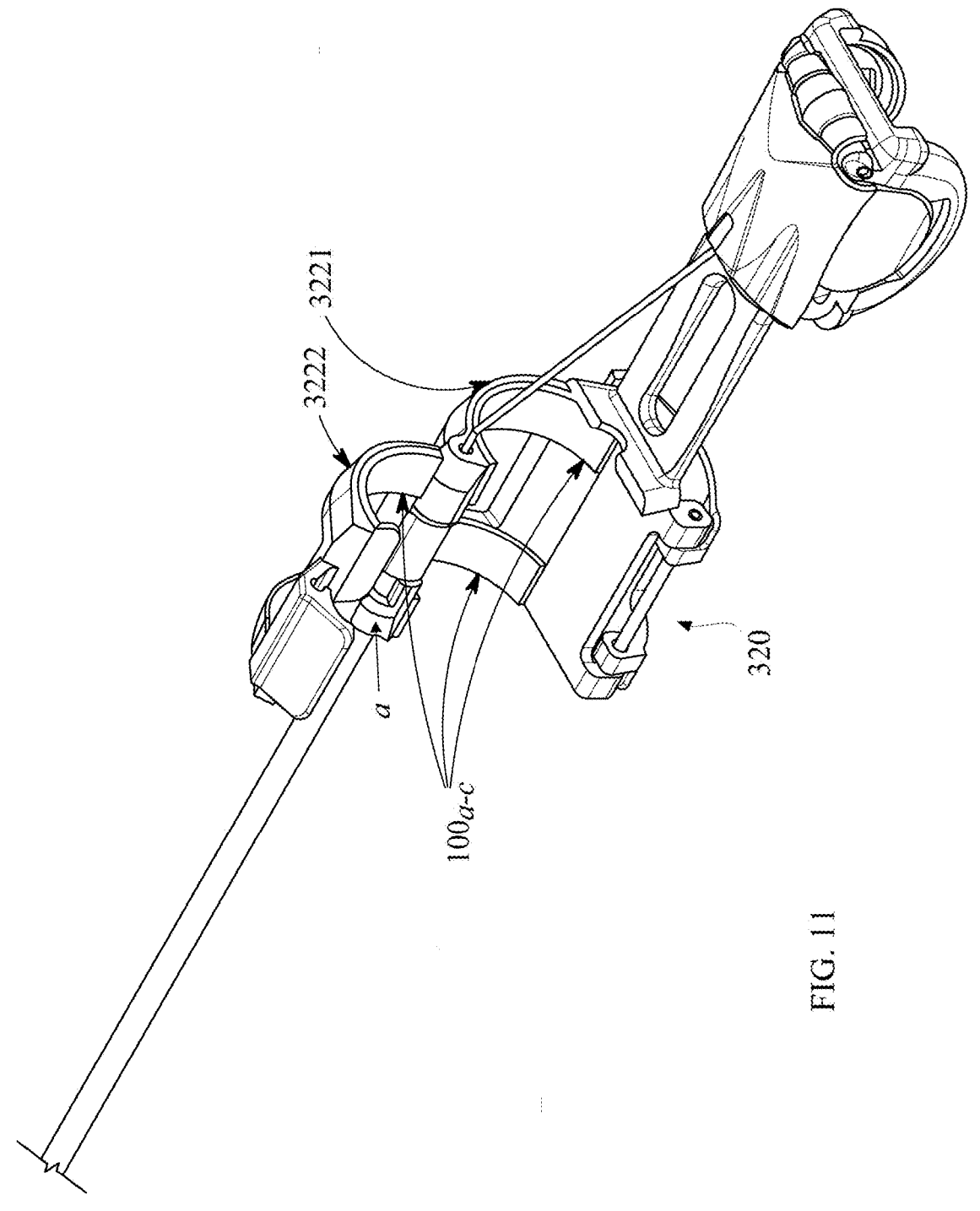
FIG. 11 illustrates a perspective view of a plurality of inner sleeve components configured for use with the ultrasound accessory of FIG. 8, according to one non-limiting aspect of the present disclosure.

Referring now to FIG. 11, a perspective view of a plurality of inner sleeve components 110$_{a-c}$ configured for use with the ultrasound accessory 320 of FIG. 8 are depicted in accordance to at least one non-limiting aspect of the present disclosure. Similar to the non-limiting aspect of FIG. 10, the plurality of inner sleeve components 110$_{a-c}$ can be collectively configured for implementation about a cylindrical instrument, such as an endoscope 200 (FIG. 8), and can have a multi-layer construction. However, according to the non-limiting aspect of FIG. 11, the sleeve 110 (FIG. 10) of the inner bushing 100 (FIG. 3) can be cut into a plurality of inner sleeve components 110$_{a-c}$ that can be separated and thus wrapped about the endoscope 200 (FIG. 8) instead of sliding the sleeve 110 (FIG. 10), in its entirety, onto the front end of the endoscope 200 (FIG. 8). Specifically, the plurality of inner sleeve components 110$_{a-c}$ of FIG. 11 are particularly configured for use with the ultrasound accessory 320 of FIG. 8. Each inner sleeve component 110$_{a-c}$ of the plurality can be configured to be coupled to a corresponding component of the ultrasound accessory 320.

Figure 12:
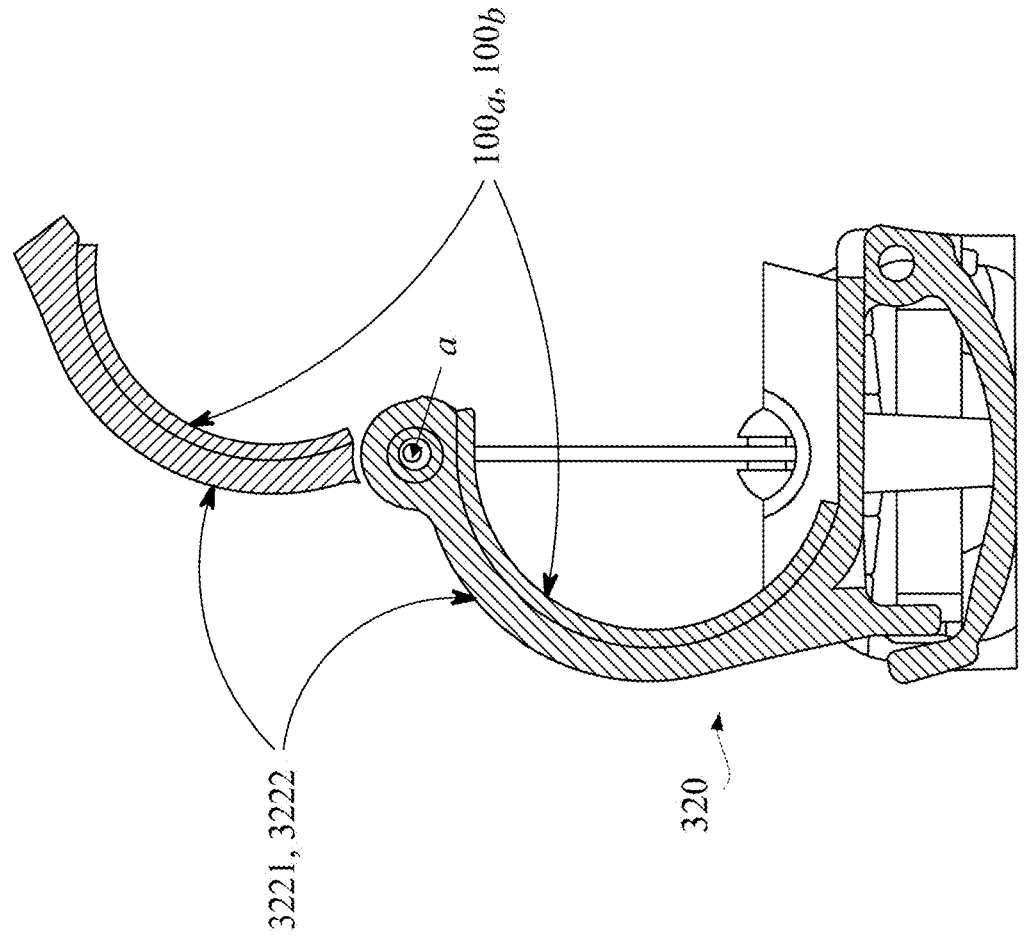
FIG. 12 illustrates a cross-sectional view of the plurality of inner sleeve components and ultrasound accessory of FIG. 11, according to one non-limiting aspect of the present disclosure.

For example, at least a subset of the plurality of inner sleeve components 110$_{a-c}$ of FIG. 11 can be configured for installation onto the first locking plate 3221 of the ultrasound accessory 320, and at least another subset of the plurality of inner sleeve components 110$_{a-c}$ can be configured for installation onto the second locking plate 3222 of the ultrasound accessory 320. As previously described, the first locking plate 3221 can be rotationally coupled to the second locking plate 3222 by a rotation shaft a, such that the ultrasound accessory 320 can be openable and closable. The first locking plate 3221—including a corresponding subset of the plurality of inner sleeve components 110$_{a-c}$—can be separated from the second locking plate 3222 and the other corresponding subset of the plurality of inner sleeve components 110$_{a-c}$. Accordingly, when installing the ultrasonic accessory 320, the plurality of inner sleeve components 110$_{a-c}$ can be closed about the endoscope 200 (FIG. 8), establishing a desired friction fit between the ultrasonic accessory 320 and the endoscope 200 (FIG. 8). However, the openable and closable nature of the ultrasonic accessory 320 and the separable nature of the plurality of inner sleeve components 110$_{a-c}$ enable the ultrasonic accessory 320 to be easily attached and removed from the endoscope 200 (FIG. 8) without complications resulting from the friction fit, which may be preferably desired during use of the ultrasonic accessory 320. This further evidenced in FIG. 12, which depicts a cross-sectional view of a first subset of the plurality of inner sleeve components 110$_a$ coupled to the first locking plate 3221 of the ultrasound accessory 320 and a second subset of the plurality of inner sleeve components 100$_b$ coupled to the second locking plate 3222 of the ultrasound accessory 320. As depicted in FIG. 12, the first locking plate 3221—including the first plurality of inner sleeve components 110$_a$—is rotatably coupled to the second locking plate 3222, including the second plurality of inner sleeve components 100$_b$. Thus, the ultrasonic accessory 320 can be easily attached and removed from the endoscope 200 (FIG. 8) while preserving the desired friction fit between the ultrasonic accessory 320 and the endoscope 200 (FIG. 8).

Examples of the method according to various aspects of the present disclosure are provided below in the following numbered clauses. An aspect of the method may include any one or more than one, and any combination of, the numbered clauses described below.

Clause 1: An inner bushing, including a sleeve and a positioning part connected at an end of the sleeve, wherein the sleeve is sleeved around an outer side wall of a distal end of an endoscope, an outer side wall of the sleeve is used for matching and connecting with a surgical attachment; the positioning part is blocked at an end face of the distal end and the positioning part is inserted into a channel of the endoscope, and the surgical attachment is aligned and connected with the positioning part.

Clause 2: The inner bushing according to clause 1, wherein the positioning part includes a connecting plate and a positioning post, wherein the connecting plate is connected to an end face of the sleeve, both ends of the positioning post is a connecting end and a free end, respectively, the connecting end is connected to a surface of a side of the connecting plate facing the sleeve, and the free end is inserted into the channel of the endoscope.

Clause 3: The inner bushing according to either of clauses 1 or 2, wherein the connecting end of the positioning post is partially exposed outside the connecting plate to form a positioning protrusion; the surgical attachment has a positioning notch, and the positioning protrusion extends into the positioning notch.

Clause 4: The inner bushing according to any of clauses 1-3, wherein the connecting plate includes a plate part and a connecting foot, the plate part extends along an end surface of the sleeve, and the connecting foot is connected between the plate part and the end surface of the sleeve.

Clause 5: The inner bushing according to any of clauses 1-4, wherein the plate part includes a main body part and a reinforcement part, and the main body part and the reinforcement part are each connected with a connecting foot; wherein the positioning post is connected with the main body part.

Clause 6: The inner bushing according to any of clauses 1-5, wherein the reinforcement part extends to connect with the main body part, or there is a gap between the reinforcement part and the main body part.

Clause 7: The inner bushing according to any of clauses 1-6, wherein one end of the connecting plate extends to protrude from a side of the sleeve, to form an easy-pull end.

Clause 8: The inner bushing according to any of clauses 1-7, wherein at least one limiting boss is provided on the outer side wall of the sleeve, the limiting boss is used to lock with the surgical attachment.

Clause 9: The inner bushing according to any of clauses 1-8, wherein two opposite sides of the outer side wall of the sleeve are both provided with the limiting boss.

Clause 10: The inner bushing according to any of clauses 1-9, wherein the sleeve is an integrally formed flexible sleeve.

Clause 11: The inner bushing according to any of clauses 1-10, wherein the sleeve includes a main body and a flexible layer, the flexible layer is attached to an inner side wall of the main body and an outer side wall of the main body.

Clause 12: An ultrasonic endoscope, including an endoscope, an ultrasonic probe and an inner bushing according to any one of clauses 1-11, the ultrasonic probe includes a probe body and an ultrasonic accessory, the ultrasonic accessory is sleeved around the outer side wall of the sleeve, and the probe body is connected with the ultrasonic accessory.

Clause 13: The ultrasonic endoscope according to clause 12, wherein the ultrasonic accessory includes a supporting plate, a locking part, a splint and a functional part, the locking part and the splint are connected respectively at two sides of the supporting plate, the locking part is sleeved around an outer side wall of the inner bushing, the probe body is locked between the splint and the supporting plate, and the functional part is connected with the supporting plate.

Clause 14: The ultrasonic endoscope according to either of clauses 12 or 13, wherein the locking part includes a first locking plate and a second locking plate, the first locking plate is fixedly connected at one side of the supporting plate, one side of the second locking plate is rotatably connected with the first locking plate, the other side of the second locking plate is locked with the other side of the supporting plate, wherein a limiting notch is provided on at least the first locking plate, and a limiting boss on the outer side wall of the sleeve is locked into the limiting notch.

Clause 15. A sleeve configured to be dispositioned between an endoscope and an ultrasound accessory selectively attachable to the endoscope, the sleeve including a rigid body including an inner surface and an outer surface, wherein the rigid body is configured to maintain a structural integrity of the sleeve, a first flexible layer positioned about the inner surface of the rigid body, wherein the first flexible layer is configured to create a friction fit between the inner surface of the rigid body and an outer surface of the endoscope, and a second flexible layer positioned about the outer surface of the rigid body, wherein the second flexible layer is configured to create a friction fit between the outer surface of the rigid body and the ultrasound accessory.

Clause 16: The sleeve according to clause 15, wherein the rigid body includes at least one of a metal, a plastic, or a composite, or combinations thereof.

Clause 17: The sleeve according to either of clauses 15 or 16, wherein the first flexible layer and the second flexible layer include at least one of a rubber, a silicone, or combinations thereof.

Clause 18: The sleeve according to any of clauses 15-17, wherein the rigid body includes a hardness that is greater than a hardness of the first flexible layer and a hardness of the second flexible layer.

Clause 19: The sleeve according to any of clauses 15-18, wherein the sleeve is a first sleeve component of a plurality of sleeve components configured to be installed within the ultrasound accessory.

Clause 20: The sleeve according to any of clauses 15-19, wherein the ultrasound accessory includes a first locking plate and a second locking plate, wherein the first locking plate is rotationally coupled to the second locking plate by a rotation shaft a, wherein the first sleeve component of the plurality of sleeve components is configured to be coupled to the first locking plate, and wherein a second sleeve component of the plurality of sleeve components is configured to be coupled to the second locking plate.

Clause 21: The sleeve according to any of clauses 15-20, wherein the ultrasound accessory comprises a second locking plate, wherein the first locking plate is rotationally coupled to the second locking plate by a rotation shaft.

Clause 22: The sleeve according to any of clauses 15-21, wherein a second sleeve component of the plurality of sleeve components is configured to be coupled to the second locking plate.

Clause 23: The sleeve according to any of clauses 15-22, wherein the ultrasound accessory further comprises a positioning plate, and wherein the sleeve is configured to be inserted into an inner bushing comprising a connecting plate configured for a particular alignment with the positioning plate such that the ultrasound accessory is properly positioned when selectively attached to the endoscope.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims), are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a"

or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures, or characteristics may be combined in any suitable manner in one or more aspects.

As used herein, the singular forms of "a", "an", and "the" include the plural references unless the context clearly dictates otherwise.

Any patent application, patent, non-patent publication, or other disclosure material referred to in this specification and/or listed in any Application Data Sheet is incorporated by reference herein, to the extent that the incorporated material is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material. None is admitted to be prior art.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. An inner bushing, comprising a sleeve and a positioning part connected at an end of the sleeve;

wherein the positioning part comprises a connecting plate and a positioning post;

wherein the sleeve is sleeved around an outer side wall of a distal end of an endoscope, an outer side wall of the sleeve is used for matching and connecting with a surgical attachment; the positioning part is blocked at an end face of the distal end and the positioning part is inserted into a channel of the endoscope, and the surgical attachment is aligned and connected with the positioning part;

wherein the connecting plate is connected to an end face of the sleeve, both ends of the positioning post is a connecting end and a free end, respectively, the connecting end is connected to a surface of a side of the connecting plate facing the sleeve, and the free end is inserted into the channel of the endoscope.

2. The inner bushing according to claim 1, wherein the connecting end of the positioning post is partially exposed outside the connecting plate to form a positioning protrusion; the surgical attachment has a positioning notch, and the positioning protrusion extends into the positioning notch.

3. The inner bushing according to claim 1, wherein the connecting plate comprises a plate part and a connecting foot, the plate part extends along an end surface of the sleeve, and the connecting foot is connected between the plate part and the end surface of the sleeve.

4. The inner bushing according to claim 3, wherein the plate part comprises a main body part and a reinforcement part, and the main body part and the reinforcement part are each connected with a connecting foot; wherein the positioning post is connected with the main body part.

5. The inner bushing according to claim 4, wherein the reinforcement part extends to connect with the main body part, or there is a gap between the reinforcement part and the main body part.

6. The inner bushing according to claim 1, wherein one end of the connecting plate extends to protrude from a side of the sleeve, to form an easy-pull end.

7. The inner bushing according to claim 1, wherein at least one limiting boss is provided on the outer side wall of the sleeve, the limiting boss is used to lock with the surgical attachment.

8. The inner bushing according to claim 7, wherein two opposite sides of the outer side wall of the sleeve are both provided with the limiting boss.

9. The inner bushing according to claim 1, wherein the sleeve is an integrally formed flexible sleeve.

10. The inner bushing according to claim 1, wherein the sleeve comprises a main body and a flexible layer, the flexible layer is attached to an inner side wall of the main body and an outer side wall of the main body.

11. An ultrasonic endoscope, comprising an endoscope, an ultrasonic probe and an inner bushing, the ultrasonic probe comprises a probe body and an ultrasonic accessory, the ultrasonic accessory is sleeved around the outer side wall of the sleeve, and the probe body is connected with the ultrasonic accessory, wherein the ultrasonic accessory comprises a supporting plate, a locking part, a splint and a functional part;

the locking part and the splint are connected respectively at two sides of the supporting plate, the locking part is sleeved around an outer side wall of the inner bushing, the probe body is locked between the splint and the supporting plate, and the functional part is connected with the supporting plate.

12. The ultrasonic endoscope according to claim 11, wherein the locking part comprises a first locking plate and a second locking plate, the first locking plate is fixedly connected at one side of the supporting plate, one side of the second locking plate is rotatably connected with the first locking plate, the other side of the second locking plate is locked with the other side of the supporting plate;

wherein a limiting notch is provided on at least the first locking plate, and a limiting boss on the outer side wall of the sleeve is locked into the limiting notch.

13. A sleeve configured to be dispositioned between an endoscope and an ultrasound accessory selectively attachable to the endoscope, the sleeve comprising:

a rigid body comprising an inner surface and an outer surface, wherein the rigid body is configured to maintain a structural integrity of the sleeve;

a first flexible layer positioned about the inner surface of the rigid body, wherein the first flexible layer is configured to create a friction fit between the inner surface of the rigid body and an outer surface of the endoscope; and a second flexible layer positioned about the outer surface of the rigid body, wherein the second flexible layer is configured to create a friction fit between the outer surface of the rigid body and the ultrasound accessory, wherein the rigid body comprises at least one of a metal, a plastic, or a composite, or combinations thereof, wherein the first flexible layer and the second flexible layer comprise at least one of a rubber, a silicone, or combinations thereof, wherein the rigid body comprises a hardness that is greater than a hardness of the first flexible layer and a hardness of the second flexible layer, wherein the sleeve is a first sleeve component of a plurality of sleeve components configured to be installed within the ultrasound accessory, wherein the ultrasound accessory comprises a first locking plate, and wherein the first sleeve component of the plurality of sleeve components is configured to be coupled to the first locking plate, wherein the ultrasound accessory comprises a second locking plate, wherein the first locking plate is rotationally coupled to the second locking plate by a rotation shaft, and wherein the ultrasound accessory further comprises a positioning plate, wherein the sleeve is configured to be inserted into an inner bushing comprising a connecting plate configured for a particular alignment with the positioning plate such that the ultrasound accessory is properly positioned when selectively attached to the endoscope.

\* \* \* \* \*